(12) United States Patent
Mori et al.

(10) Patent No.: US 6,555,119 B1
(45) Date of Patent: Apr. 29, 2003

(54) TRANSPARENT MICRO EMULSION

(75) Inventors: Kiyoaki Mori, Yokaichi (JP); Hidekazu Tanaka, Shiga (JP); Shuichi Tsunetsugu, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/936,406

(22) PCT Filed: Apr. 14, 1999

(86) PCT No.: PCT/US99/08233

§ 371 (c)(1),
(2), (4) Date: Sep. 11, 2001

(87) PCT Pub. No.: WO00/61083

PCT Pub. Date: Oct. 19, 2000

(51) Int. Cl.[7] .............................. A61K 7/00; A61K 7/42; A61K 7/44; A61K 7/06
(52) U.S. Cl. ........................... 424/401; 424/59; 424/60; 424/70.1; 424/70.12; 424/70.13; 424/70.19; 424/70.21; 424/70.27; 424/70.31
(58) Field of Search ................................ 424/401, 70.1, 424/70.31, 70.12

(56) References Cited

U.S. PATENT DOCUMENTS

| | | | | | |
|---|---|---|---|---|---|
| 4,650,827 A | * | 3/1987 | Becker et al. | ............... | 524/801 |
| 4,710,373 A | * | 12/1987 | Nakamura et al. | ............ | 424/59 |
| 4,824,602 A | * | 4/1989 | Juneja | ........................ | 252/547 |
| 5,017,365 A | * | 5/1991 | Niedbala | ..................... | 424/59 |
| 5,171,782 A | * | 12/1992 | Candau et al. | .............. | 524/801 |
| 5,207,998 A | * | 5/1993 | Robinson et al. | .............. | 424/59 |

FOREIGN PATENT DOCUMENTS

| | | |
|---|---|---|
| DE | 4039063 A | 6/1992 |
| DE | 19710155 A | 9/1998 |
| EP | 0 214626 A | 3/1987 |
| EP | 0 760237 A | 3/1997 |

* cited by examiner

Primary Examiner—Thurman K. Page
Assistant Examiner—Micah-Paul Young
(74) Attorney, Agent, or Firm—John M. Howell; Armina E. Matthews; Tara M. Rosnell

(57) ABSTRACT

A transparent micro-emulsion including two or more non-ionic surfactants, two or more oily components, a water-soluble high molecular weight polymer, and a cosmetically acceptable carrier. The sum of the concentration of the surfactants (a) and the oily components (b) is less than about 0.6 wt %. The ratio of the surfactant to the oily component is from about 2:1 to about 1:1.

10 Claims, No Drawings

TRANSPARENT MICRO EMULSION

CONTINUATION DATA

This application is filed under 35 U.S.C. 371, which is the national stage of PCT/US99/08233 filed on Apr. 14, 1999.

FIELD

The present invention relates to a transparent micro emulsion. In particular, it relates to a transparent micro emulsion for skin moisturizing, smoothness, and softness.

BACKGROUND

Many personal care products currently available to consumers are directed primarily to improving the health and/or physical appearance of the skin. Among these skin care products, many are directed to delaying, minimizing or even eliminating skin wrinkling and other histological changes typically associated with skin aging or environmental damage to human skin such as wrinkling and other forms of roughness (including increased pore size, flaking and skin lines). In order to maintain or return skin to a healthy and/or youthful state, the skin is typically treated with products containing a moisturizing agent. Generally, the greater the concentration of moisturizing agents the more the moisturization effect to the skin.

Oil-in-water and/or water-in-oil emulsions are well-known. In particular, cosmetic products that can be supplied in emulsion form include lotions, tonics, serums or toilet waters and also include transparent and semi-transparent types. Such emulsions, particularly transparent lotions, are preferable for use in skin care products in order to provide moistness and softness to the skin, while not causing skin greasiness or stickiness. However, the higher concentration of moisturizing agents in such compositions and/or emulsions tends to cause the loss of transparency of the compositions and/or emulsions and may further cause separation of oil and water content as well as sticky and greasy feeling of skin. The lower the moisturizing agents levels, e.g., oily components, the lower the moisturizing efficacy to the skin. It is also known in the arts that certain surfactants are useful for emulsifying oily materials, but increasing the levels in emulsion may cause irritation of skin.

Based on the foregoing, there is a need to seek a transparent emulsion for improving one's skin condition by maximizing the amount of moisturizing agent in the composition and/or improving the spreadability of the moisturizing agent to the skin, yet continue to impart a non-greasy feeling to the user.

SUMMARY

The present invention is directed to a transparent micro emulsion comprising:

(a) two or more nonionic surfactants selected from the group consisting of polyoxyalkylene alkyl ether having the $C_{12-18}$ of alkyl substitute, polyoxyalkylene hydrogenated castor oil, and a linear or branched, mono- or tri-alkyl glyceride;

(b) two or more oily components selected from the group consisting of hydrocarbon oils, fatty acid esters, and silicone oils;

(c) a water-soluble high molecular weight polymer; and (d) a cosmetically-acceptable carrier comprising a polyol and water.

The sum of the concentration of the surfactants and the oily components is less than about 6.0 wt %. The ratio of the surfactants to the oily components is from about 2:1 to about 1:1.

These and other features, aspects, and advantages of the present invention will become better understood from a reading of the following description, and appended claims.

DETAILED DESCRIPTION

While the specification concludes with claims particularly pointing out and distinctly claiming the invention, it is believed that the present invention will be better understood from the following description.

All percentages, ratios, and levels of ingredients referred to herein are based on the actually total amount of the composition and/or emulsion, unless otherwise indicated.

All measurements referred to herein are made at 25° C. unless otherwise specified.

All publications, patent applications, and issued patents mentioned herein are hereby incorporated in their entirety by reference. Citation of any reference is not an admission regarding any determination as to its availability as prior art to the claimed invention.

Herein, "comprising" means that other steps and other ingredients which do not affect the end result can be added. This term encompasses the terms "consisting of" and "consisting essentially of."

Herein, "topical application" means to apply or spread a material onto the surface of the skin.

Herein, "cosmetically-acceptable carrier," means one or more compatible dermatologically-acceptable solid or liquid filler diluents or encapsulating substances.

Herein, "dermatologically-acceptable," means that the compositions and/or emulsions or components thereof so described are suitable for use in contact with human skin without undue toxicity, incompatibility, instability, irritation allergic response, and the like, commensurate with a reasonable benefit/risk ratio.

Herein, "safe and effective amount," means an amount of a compound or composition/emulsion sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound judgment of the skilled artisan.

Herein, "mixtures" is meant to include a simple combination of materials and any compounds that may result from their combination.

All ingredients such as actives and other ingredients useful herein may be categorized or described by their cosmetic and/or therapeutic benefit or their postulated mode of action. However, it is to be understood that the active and other ingredients useful herein can, in some instances, provide more than one cosmetic and/or therapeutic benefit or operate via more than one mode of action. Therefore, classifications herein are made for the sake of convenience and are not intended to limit an ingredient to the particularly stated application or applications listed.

A. Transparent Micro Emulsion

The transparent micro emulsion of the present invention includes two or more nonionic surfactants, two or more oily components, a water-soluble high molecular weight polymer, and a cosmetically-acceptable carrier. The sum of the concentration of the surfactants (a) and the oily components (b) is less than about 6.0 wt %. The ratio of the surfactants to the oily components is from about 2:1 to about 1:1. Preferably, the transparent micro emulsion of the present invention is a dermatologically-acceptable topical composition; more preferably a cosmetic composition.

Herein, "transparent" means that emulsions have sufficient transparency to see the other side through the emulsion in a clear glass or plastic bottle. Herein, "micro emulsion" means a solution in which oil and water, form micelle structures, that are dispersed in solution and such dispersion is stable over time. Preferably, the droplets present in the emulsions are a mean particle size of less than about 100 m$\mu$ meter (0.1 $\mu$m=100 nm) of; more preferably less than about 80 m$\mu$ meter (0.08 $\mu$m). Herein, "droplets," refer to an emulsion particle wherein the water and the oily component are absorbed together through a surfactant. It is believed that the droplets' particle size affect the transparency and turbidity of the emulsion and/or composition which contains oil, surfactants, and water. When the emulsion has droplets which are large in size, particularly more than 0.1 $\mu$m, the emulsion tends to be turbid, e.g., not clear. The size of the droplets can be determined using a Laser Scattering Particle Size Distribution Analyzer LA-910 by Horiba (Japan). The size of droplets is measured with the emulsion at a temperature of 25° C.+/−1° C., after 30 seconds mixing.

In another aspect, the transparent micro emulsion of the present invention, having the specific combination of more than two surfactants and oily components has an absorbent value of less than about 2 at a wave length of 340 nm; preferably from about 1 to about 1.5 at the same wave length. An emulsion having an absorbent value of greater than 2 at the above wave length tends to be insufficiently transparent.

The transparent micro emulsion of the present invention, preferably, contains less than 6.0 wt % of the sum of the surfactant (a) and the oily components (b); more preferably less than 3.0 wt %. The ratio of the surfactant to the oily component is from about 2:1 to about 1:1.

B. Surfactants

The transparent micro emulsion of the present invention contains two or more nonionic surfactants selected from the group consisting of polyoxyalkylene alkyl ether having the $C_{12-18}$ of alkyl substitute, polyoxyalkylene hydrogenerated castor oil, and a liner or branched, mono- or tri-alkyl glyceride. Preferably, at least one of the nonionic surfactant has a hydrophilic-lipophilic balance (HLB) of more than 10 and at least one of the nonionic surfactant has an HLB of less than 10.

Generally, lower HLB components have a larger solubilizing capacity with water and higher HLB components are effective for mixing with oily components. Without being bound by the theory, it is believed that the low levels of nonionic surfactant, having low HLB, can be mixed with water for preparing uniform surfactants-water solution. It is also believed that such mixture can facilitate to mix with oily components, with surfactants having high HLB which are added before the oily components, for preparation of uniform emulsion. Preferably, the emulsion of the present invention contains a large amount of the nonionic surfactants having high HLB than that having low HLB.

Polyoxyalkylene alkyl ether useful herein are the condensation products of alkylene oxides with both fatty acids and fatty alcohols (e.g., wherein the polyalkylene oxide portion is esterified on one end with a fatty acid and etherified (e.g., connected via an ether linkage) on the other end with a fatty alcohol). These materials have the general formula $R^1CO(X_1)zOR^2$ wherein $R^1$ and $R^2$ are independently alkyl of from about 12 to about 18 carbons; $X_1$ is —$OCH_2CH_2$ derived from, for example ethylene glycol or —$OCH_2CHCH_3$— derived from propylene glycol or oxide; and z is an integer from about 6 to about 50.

Nonlimiting examples of such alkylene oxide derived nonionic surfactants include ceteth-6, ceteth-10, ceteth-12, ceteareth-6, ceteareth-10, ceteareth-12, ceteareth-20, ceteareth-30, steareth-6, steareth-10, steareth-1 2, steareth-20, PEG-100 steareth, PEG-6 stearate, PEG-10 stearate, PEG-12 stearate, PEG-100 stearate, PEG-10 glyceryl stearate, PEG-20 glyceryl stearate, PEG-30 glyceryl cocoate, PEG-80 glyceryl cocoate, PEG-80 glyceryl tallowate, PEG-200 glyceryl tallowate, PEG-8 dilaurate, PEG-10 distearate, and mixtures thereof; preferably, ceteareth-12, ceteareth-20, and ceteareth-30.

Examples of polyoxyalkylene hydrogenerated castor oil useful herein includes polyethylene hydrogenerated caster oil; preferably polyethylene (20) hydrogenerated caster oil.

Examples of mono- or tri-alkyl glyceride useful herein includes glyceryl monostearate, glyceryl oleate, and triglyceryl diisostearate; preferably triglyceryl diisostearate.

Preferably, the total concentration of the nonionic surfactants are from about 0.2 wt % to about 2 wt %, preferably from about 0.6% to about 1.2%

C. Oily Component

The transparent micro emulsion of the present invention includes two or more oily components selected from the group consisting of hydrocarbon oils, fatty acid esters, and silicone oils. The oily components useful herein provides moisturizing efficacy to the skin.

A wide variety of suitable oil compounds are known and may be used herein and numerous examples can be found in Sagarin, Cosmetics, Science and Technology, 2nd Edition, Vol. 1, pp. 32–43 (1972). Nonlimiting examples of suitable oily components include $C_{1-30}$ alcohol esters of $C_{1-30}$ carboxylic acids and of $C_{2-30}$ dicarboxylic acids, hydrocarbon oils, Mono-, di- and tri-glycerides of $C_{1-30}$ carboxylic acids, silicone oils, mineral oil and petrolatums, vegetable oils and hydrogenated vegetable oils, animal fats and oils, silicone oils, and mixture thereof; preferably hydrocarbon oils, triglycerides, and silicone oils. Preferred ester include cetyl 2-ethyl hexyl, isopropyl myristate, myristyl myristate, isopropyl palmitate, cholesterol; more preferably cetyl 2-ethyl hexyl and myristyl myristate.

Hydrocarbon oils useful herein includes these having from about 7 to about 40 carbons. Examples of these hydrocarbon materials include dodecane, isododecane, squalane, hydrogenated polyisobutylene, docosane (i.e., a $C_{22}$ hydrocarbon), hexadecane, isohexadecane. Also useful are the $C_{7-40}$ isoparaffins, which are $C_{7-40}$ branched hydrocarbons. Preferred hydrocarbon oils are squalane, light paraffin, light isoparaffin, light liquid paraffin, light liquid isoparaffin (a commercially available hydrocarbon sold as Isoper G® by Exxon, Isoparaffin® 2028 by ldemitsu, Amsco Mineral Spirits® by Ashland). Preferred triglycerides includes caprylic/capric triglyceride, PEG-6 caprylic/capric triglyceride, and PEG-8 caprylic/capric triglyceride, Meadowfoam Seed Oil.

Silicone oils useful herein may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable silicone oils can be selected from a wide variety of silicones spanning a broad range of volatilities and viscosities. Nonvolatile polysiloxanes are preferred. Nonlimiting examples of suitable silicones are disclosed in U.S. Pat. No. 5,069,897, to Orr, issued Dec. 3, 1991, which is incorporated by reference herein in its entirety. Examples of suitable silicone oils include polyalkylsiloxanes, cyclic polyalkylsiloxanes, and polyalkylarylsiloxanes.

Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Suitable dimethicones include those alkyl-substituted dimethicones include cetyl dimethicone and lauryl dimethicone. Commercially available dimethiconols are typically sold as mixtures with dimethicone or cyclomethicone (e.g., Dow Corning® 1401 and 1403 fluids). Cyclic polyalkylsiloxanes suitable for use and commercially available include Dow Corning® 244 fluid, Dow Corning® 344 fluid, Dow Corning® 245, and Dow Corning® 345 fluid.

The ratio of the oily components to the surfactants are from about 1:1 to about 1:2. Preferably, the oily components are present in a concentration of less than 3.0 wt % in the emulsion, more preferably, from about 0.5 to about 2.0 wt %.

D. Water-Soluble High Molecular Weight Polymer

The transparent micro emulsions of the present invention include a water-soluble high molecular weight polymer. Preferably, the water-soluble polymer is present from about 0.0001% to about 0.2% by weight, more preferably from about 0.001% to about 0.1% in the emulsion.

It is believed that a higher level of the water-soluble polymers useful herein will result in an undesirably tacky or sticky feeling emulsion and a lower level may result in insufficient moisturization and smoothness of the skin.

Water-soluble polymers useful herein include polysaccharides, gums, mucopolysaccharides (e.g., hyaluronic acid, chondroitin sulfate), carboxylic acid polymers, alkyl acrylate and acric acid copolymer, crosslinked polyacrylate polymers, and mixtures thereof; preferably polysaccharides, gums, or mixtures thereof.

Extract materials which are derived from natural sources (e.g., Quince Seed and Sea Weed) can be included as water-soluble polymers. Quince Seed is available from Taiyo Kagaku (Mie prefecture, Japan). Examples of suitable water-soluble polymers for use herein are listed below.

1. Polysaccharide.

A wide variety of polysaccharides can be used in the emulsion of the present invention. Herein, "polysaccharides" refers to thickening agents containing a backbone of repeating sugar (e.g., carbohydrate) units. Nonlimiting examples of useful polysaccharides include those selected from the group consisting of cellulose, carboxymethyl hydroxyethylcellulose, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, pullulan, mannan, tolehalose, and mixtures thereof; more preferably hydroxypropylcellulose.

In the above examples of useful polysaccharides, the hydroxy groups of the cellulose polymer are preferably hydroxyalkylated (preferably hydroxyethylate or hydroxypropylate), forming a hydroxyalkylated cellulose that is further modified with a straight or branched alkyl group of from about 10 to about 30 carbons through an ether linkage. Preferred polysaccharides are ethers of straight or branched alcohols of from about 10 to about 30 carbons with hydroxyalkylcelluloses.

Additional examples of useful polysaccharides include alkyl substituted cellulose. Nonlimiting examples of the alkyl groups useful herein include stearyl, isostearyl, lauryl, myristyl, cetyl, isocetyl, cocoyl (e.g., alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers herein is the material given the CTFA designation cetyl hydroxyethylcellulose, which is the ether of cetyl alcohol and hydroxyethylcellulose. This material is sold under the tradename Natrosol® CS Plus from Aqualon Corporation (Willmington, U.S.A.).

Other polysaccharides useful herein include scleroglucans containing a linear chain of (1 to less than 3) linked glucose units with a (1 to less than 6) linked glucose every three units. A commercially available example of this is Clearogel™ CS11 from Michel Mercier Products Inc. (Mountainside, N.J., U.S.A.).

2. Gum

Other water-soluble polymers which can be employed in the emulsion include materials which are primarily derived from natural sources. Nonlimiting examples of such water-soluble polymers include gums selected from the group consisting of acacia, agar, algin, alginic acid, ammonium alginate, amylopectin, calcium alginate, calcium carrageenan, camitine, carrageenan, dextrin, gelatin, gellan gum, guar gum, guar hydroxypropyltrimonium chloride, sodium hyaluroinate, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Additional polymers which are suitable herein as water-soluble polymers include those disclosed in U.S. Pat. No. 4,387,107, to Klein et al., issued Jun. 7, 1983 and "Encyclopedia of Polymer and Thickeners for Cosmetics," R. Y. Lochhead and W. R. Fron, eds., *Cosmetics & Toiletries*. vol. 108, pp. 95–135 (May 1993).

D. Cosmetically-Acceptable Carrier

The emulsion of the present invention contains a cosmetically-acceptable carrier. The carrier used herein can act as a solvent for one or more of the other components of the emulsion. Preferably, the cosmetically-acceptable carrier includes a polyol and water. The cosmetically-acceptable carrier is present from about 80% to about 98.0% in the emulsion; preferable from about 90% to about 95%.

Preferably, the polyols useful herein include, but are not limited to, polyalkylene glycols, more preferably alkylene polyols and their derivatives including glycerin, propylene glycol, dipropylene glycol, tripropylene glycol, 1.2-pentane diol, polyethylene glycol and derivatives thereof, sorbitol, hydroxypropyl sorbitol, erythritol, threitol, pentaerythritol, xylitol, glucitol, mannitol, hexylene glycol, 1,3-butylene glycol, 1,2,6-hexanetriol, glycerol, ethoxylated glycerol, propoxylated glycerol, sodium 2-pyrrolidone-5-carboxylate, soluble collagen, gelatin, 1.2-pentandiol, and mixtures thereof. Preferred polyols are glycerin, 1,3-butylene glycol, glucose, lactic acid, trimethylglycine, urea, or mixtures thereof; more preferably glycerin or 1,3-butylene glycol. The polyols are present in the emulsion from about 0.01% to about 20.0%, preferably from about 8.0% to about 15.0%.

The concentration of water in the present emulsion is from about 60 wt % to about 95.0 wt % by weight, preferably from about 80 wt % to about 90 wt %. In one embodiment, the carrier can further includes a lower alkyl alcohols. The lower alkyl alcohols, if present in the emulsion, are $C_1$–$C_6$ alkyl monohydric alcohols; preferably $C_2$–$C_3$ alkyl alcohols. Preferred lower alkyl alcohols include ethyl alcohol, isopropyl alcohol, and mixtures thereof.

E. Optional Components

The transparent micro emulsion of the present invention may further comprises optional components. Herein, "optional components" means one or more compatible solid or liquid fillers, diluents, extenders and the like, which are commonly used in cosmetics as defined herein. The term "compatible" herein means that the components of the emulsions of this invention are capable of being commingled with each other, in a manner such that there is no interaction which would substantially reduce the efficacy of the emulsion under ordinary use situations.

Optional components useful herein include a pH adjuster and an active. The type of the optional component utilized in the present invention depends on the type of the product desired and may comprise several types of carriers including, but not limited to, oil-in-water or water-in-oil emulsion.

1) pH Adjuster

The optional component can be a pH adjuster. Herein, "pH adjuster" refers to any component which is employed to increase or decrease the overall pH of the composition/emulsion to an optimum pH, thereby preventing undesirable skin feeling such as skin irritation. An optimum pH is subject to the selection of preventing skin irritation. Preferably, the optimum pH is around 5.0 to about 7.0. Suitable pH adjusters herein include acetate, phosphate, citrate, triethanolamine and carbonate. A combination of the foregoing are often employed to adjust to a specific optimal pH for the composition/emulsion. The total level of the pH adjuster is from about 0.01% to about 5.0%, preferably, from about 0.5% to about 2.0%.

2) Actives

The optional component useful herein can also contain actives. Examples of such actives include, but are not limited to, a vitamin $B_3$ compound, anti-oxidants and radical scavengers, anti-inflammatory agents, antimicrobial agents, sunscreens and sunblocks, and chelators. Other actives useful herein include vitamin A (e.g., retinoid which are commercially available from a number of sources, for example, Sigma Chemical Company (St. Louis, Mo.), and Boerhinger Mannheim (Indianapolis, Ind.) and described in U.S. Pat. No. 4,677,120, Parish et al., issued Jun. 30, 1987; U.S. Pat. No. 4,885,311, Parish et al., issued Dec. 5, 1989; U.S. Pat. No. 5,049,584, Purcell et al., issued Sep. 17, 1991; U.S. Pat. No. 5,124,356, Purcell et al., issued Jun. 23, 1992; and Reissue Patent 34,075, Purcell et al., issued Sep. 22, 1992); and vitamin K.

(i) Vitamin $B_3$ Compounds: The vitamin $B_3$ compound enhances the skin appearance benefits of the present invention, especially in improving skin condition, including treating signs of skin aging, more especially wrinkles, lines, and pores. The vitamin $B_3$ compound is preferably present from about 0.01% to about 50%, more preferably from about 0.1% to about 10%, even more preferably from about 0.5% to about 10%, and still more preferably from about 1% to about 5%.

Herein, "vitamin $B_3$ compound" means a compound having the formula:

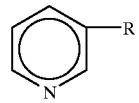

wherein R is —$CONH_2$ (e.g., niacinamide), —COOH (e.g., nicotinic acid) or —$CH_2OH$ (e.g., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Suitable esters of nicotinic acid include nicotinic acid esters of from 1 to about 22 carbons, preferably 1 to about 16 carbons, more preferably alcohols from about 1 to about 6 carbons. The alcohols are suitably straight-chain or branched chain, cyclic or acyclic, saturated or unsaturated (including aromatic), and substituted or unsubstituted. The esters are preferably non-vasodilating. As used herein, "non-vasodilating" means that the ester does not commonly yield a visible flushing response after application to the skin in the subject compositions/emulsions (the majority of the general population would not experience a visible flushing response, although such compounds may cause vasodilation not visible to the naked eye, i.e., the ester is non-rubifacient). Non-vasodilating esters of nicotinic acid include tocopherol nicotinate and inositol hexanicotinate; tocopherol nicotinate is preferred.

Other derivatives of the vitamin $B_3$ compound are derivatives of niacinamide resulting from substitution of one or more of the amide group hydrogens. Nonlimiting examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., 1 to about 18 carbons). Specific examples of such derivatives include nicotinuric acid ($C_8H_8N_2O_3$) and nicotinyl hydroxamic acid ($C_6H_6N_2O_2$), which have the following chemical structures: nicotinuric acid:

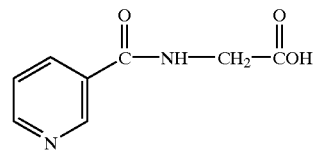

nicotinyl hydroxamic acid:

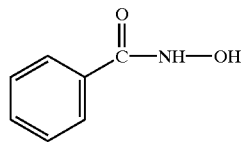

Exemplary nicotinyl alcohol esters include nicotinyl alcohol esters of the carboxylic acids salicylic acid, acetic acid, glycolic acid, palmitic acid and the like. Other non-limiting examples of vitamin $B_3$ compounds useful herein are 2-chloronicotinamide, 6-aminonicotinamide, 6-methylnicotinamide, n-methyl-nicotinamide, n,n-diethyinicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, and niaprazine.

Nonlimiting examples of the above vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

One or more vitamin B3 compounds may be used herein. Preferred vitamin $B_3$ compounds are niacinamide and tocopherol nicotinate. Niacinamide is more preferred.

When used, salts, derivatives, and salt derivatives of niacinamide are preferably those having substantially the same efficacy as niacinamide in the methods of regulating skin condition described herein.

Salts of the vitamin $B_3$ compound are also useful herein. Nonlimiting examples of salts of the vitamin $B_3$ compound useful herein include organic or inorganic salts, such as inorganic salts with anionic inorganic species (e.g., chloride, bromide, iodide, carbonate, preferably chloride), and organic carboxylic acid salts (including mono-, di- and tri-$C_{1-18}$ carboxylic acid salts, e.g., acetate, salicylate, glycolate, lactate, malate, citrate, preferably monocarboxylic acid salts such as acetate). These and other salts of the vitamin $B_3$ compound can be readily prepared by the skilled artisan, for example, as described by W. Wenner, "The Reaction of L-Ascorbic and D-losascorbic Acid with Nicotinic Acid and Its Amide", J. Organic Chemistry, Vol. 14, 22–26 (1949). Wenner describes the synthesis of the ascorbic acid salt of niacinamide.

In a preferred embodiment, the ring nitrogen of the vitamin $B_3$ compound is substantially chemically free (e.g., unbound and/or unhindered), or after delivery to the skin becomes substantially chemically free ("chemically free" is hereinafter alternatively referred to as "uncomplexed"). More preferably, the vitamin $B_3$ compound is essentially uncomplexed. Therefore, if the emulsion contains the vitamin $B_3$ compound in a salt or otherwise complexed form, such complex is preferably substantially reversible, more preferably essentially reversible, upon delivery of the emulsion to the skin. For example, such complex should be substantially reversible at a pH of from about 5.0 to about 6.0. Such reversibility can be readily determined by one having ordinary skill in the art.

More preferably the vitamin $B_3$ compound is substantially uncomplexed in the emulsion prior to delivery to the skin. Exemplary approaches to minimizing or preventing the formation of undesirable complexes include omission of materials which form substantially irreversible or other complexes with the vitamin $B_3$ compound, pH adjustment, ionic strength adjustment, the use of surfactants, and formulating wherein the vitamin $B_3$ compound and materials which complex therewith are in different phases. Such approaches are well within the level of ordinary skill in the art.

Thus, in a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably essentially free of the salt form. The vitamin $B_3$ compound in the emulsions hereof having a pH of from about 4 to about 7 typically contain less than about 50% of the salt.

The vitamin $B_3$ compound may be included as the substantially pure material, or as an extract obtained by suitable physical and/or chemical isolation from natural (e.g., plant) sources. The vitamin $B_3$ compound is preferably substantially pure, more preferably essentially pure.

(ii) Anti-Oxidants and Radical Scavengers: Anti-oxidants and radical scavengers are especially useful for providing protection against UV radiation which can cause increased scaling or texture changes in the stratum comeum and against other environmental agents which can cause skin damage.

Anti-oxidants and radical scavengers such as tocopherol (vitamin E), tocopherol sorbate, tocopherol acetate, other esters of tocopherol, propyl gallate, alkyl esters of uric acid, amines (i.e., N,N-diethylhydroxylamine, amino-guanidine), sulfhydryl compounds (i.e., glutathione), lycine pidolate, arginine pilolate, bioflavonoids, lysine, methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical emulsions and applicable to the present invention is described in U.S. Pat. No. 4,847,071, Bissett et al, issued Jul. 11, 1989.

(iii) Anti-Inflammatory Agents: Anti-inflammatory agents enhance the skin appearance benefits, by for example, contribution of uniformity and acceptable skin tone and/or color.

Preferably, the anti-inflammatory agent includes a steroidal anti-inflammatory agent and an non-steroidal anti-inflammatory agent. Preferred steroidal anti-inflammatory for use is hydrocortisone.

The variety of compounds encompassed by this group are well-known to those skilled in the art. For detailed disclosure of the chemical structure, synthesis, side effects, etc. of non-steroidal anti-inflammatory agents, reference may be had to standard texts, including Anti-inflammatory and Anti-Rheumatic Drugs, K. D. Rainsford, Vol. I–III, CRC Press, Boca Raton, (1985), and Anti-inflammatory Agents, Chemistry and Pharmacology, 1, R. A. Scherrer, et al., Academic Press, New York (1974), each incorporated herein by reference.

So-called "natural" anti-inflammatory agents are also useful. Such agents may suitably be obtained as an extract by suitable physical and/or chemical isolation from natural sources (i.e., plants, fungi, by-products of microorganisms). For example, alpha bisabolol, aloe vera, Manjistha (extracted from plants in the genus Rubia, particularly *Rubia Cordifolia*), and Guggal (extracted from plants in the genus Commiphora, particularly *Commiphora Mukul*), kola extract, chamomile, and sea whip extract, may be used.

(iv) Antimicrobial Agent: As used, "antimicrobial agents" means a compound capable of destroying microbes, preventing the development of microbes or preventing the pathogenic action of microbes. Antimicrobal agents are useful, for example, in controlling acne. Preferred antimicrobial agents useful in the present invention are benzoyl peroxide, erythromycin, tetracycline, clindamycin, azelaic acid, sulfur resorcinol, phenoxyethanol, and Irgasan™ DP 300 (Ciba Geigy Corp., U.S.A.). A safe and effective amount of an antimicrobial agent may be added to emulsions of the present invention, preferably from about 0.001% to about 10%, more preferably from about 0.01% to about 5%, still more preferably from about 0.05% to about 2%.

(v) Sunscreens and Sunblocks: Sunscreens and sunblocks generally prevent excessive scaling and texture changes of the stratum corneum by exposure of ultraviolet light and may be added to the emulsion of the present invention. Suitable sunscreens and sunblocks may be organic or inorganic.

A wide variety of conventional sunscreens and sunblocks are suitable for use herein. See, U.S. Pat. No. 5,087,445, Haffey et al, issued Feb. 11, 1992; U.S. Pat. No. 5,073,372, Turner et al, issued Dec. 17, 1991; U.S. Pat. No. 5,073,371, Turner et al., issued Dec. 17, 1991; and Segarin, et al, at Chapter VIII, pages 189 et seq., of Cosmetics Science and Technology (1972), which discloses numerous suitable sunscreens and sunblocks. Preferred among those sunscreens and sunblocks which are useful in the emulsions are those selected from 2-ethylhexyl-p-methoxycinnamate (commercially available as PARSOL MCX), butylmethoxydibenzoyl-methane, 2-hydroxy4-methoxybenzo-phenone, 2-phenylbenzimidazole-5-sulfonic acid, octyidimethyl-p-aminobenzoic acid, octocrylene, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyidibenzoylmethane, 4-isopropyl dibenzoylmethane, 3-benzylidene camphor, 3-(4-methylbenzylidene) camphor, titanium dioxide, zinc oxide, silica, iron oxide, Eusolex™ 6300, Octocrylene, Parsol 1789, and mixtures thereof.

Also particularly useful in the emulsions are sunscreens and sunblocks such as those disclosed in U.S. Pat. No. 4,937,370, Sabatelli, issued Jun. 26, 1990, and U.S. Pat. No. 4,999,186, Sabatelli, issued Mar. 12, 1991. The sunscreens and sunblocks disclosed therein have, in a single molecular, two distinct chromophore moieties which exhibit different ultraviolet radiation absorption spectra. One of the chromophore moieties absorbs predominantly in the UVB radiation range and the other absorbs strongly in the UVA radiation range. These sunscreens and sunblocks provide higher efficacy, broader UV absorption, lower skin penetration and longer lasting efficacy relative to conventional sunscreens and sunblocks.

Exact amounts will vary depending upon the sunscreen chosen and the desired Sun Protection Factor (SPF). SPF is a commonly used measure of photoprotection of a sunscreen against erythema. See Federal Register, Vol. 43, No. 166, pp. 38206–38269, Aug. 25, 1978.

A sunscreen or sunblock herein may also be added to improve the skin, particularly to enhance their resistance to being washed off by water, or rubbed off. Preferred sunscreens and sunblocks which will provide this benefit are a copolymer of ethylene and acrylic acid. Emulsions comprising this copolymer are disclosed in U.S. Pat. No. 4,663,157, Brock, issued May 5, 1987.

(vi) Chelators: As used herein, "chelator" refers to a compound that reacts for removing a metal ion from a system by forming a complex so that the metal ion cannot readily participate in or catalyze chemical reactions. The inclusion of a chelator is especially useful for providing protection against UV radiation which can contribute to excessive scaling or skin texture changes and against other environmental agents which can cause skin damage.

Exemplary chelators that are useful herein are disclosed in U.S. Pat. No. 5,487,884, Bissett et al, issued Jan. 30, 1996; PCT application 91/16035 and 91/16034, Bush et al, published Oct. 31, 1995. Preferred chelators are furildioxime and derivatives thereof.

3) Other Optional Components

In addition to the above described components, the emulsion of the present invention may further include preservatives and preservative enhancers such as water-soluble or solubilizable preservatives including Germall 115, methyl, ethyl, propyl and butyl esters of hydroxybenzoic acid, benzyl alcohol, EDTA, Bronopol (2-bromo-2-nitropropane-1,3-diol) and phenoxypropanol; antifoaming agents; binders; biological additives; bulking agents; coloring agents; perfumes, essential oils, and solubilizers thereof; natural extracts; compounds which stimulate collagen production.

F. Method for Making Composition

The emulsions of the present invention are generally prepared by any method conventionally used for providing skin care compositions/emulsions, particularly for skin lotions and micro emulsion that are known in the art. Such methods typically involve mixing of the ingredients in one or more steps to a relatively uniform state, with or without heating, cooling, high share mixing, and the like. Typical methods are described in, for example are described in Harry's Cosmeticology, 7th Ed., Harry & Wilkinson (Hill Publishers, London 1982).

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Examples 1–3

Examples 1–3 of the transparent micro emulsion of the present invention are prepared from the following ingredients by the formulating techniques set forth below.

| Phase | | (unit weight %) | | |
|---|---|---|---|---|
| | | 1 | 2 | 3 |
| A | Ceteareth-12[1] | 0.02 | 0.04 | 0.020 |
| A | Ceteareth-20[2] | 0.13 | 0.14 | 0.054 |
| A | Ceteareth-30[3] | 0.15 | 0.24 | 0.097 |
| A | triglyceryl diisostearate | 0.32 | 0.39 | 0.156 |
| A | POE(20) hydrogenated castor oil | 0.15 | 0.12 | 0.048 |
| A | cetyl 2-ethyl hexyl | 0.23 | 0.07 | 0.028 |
| A | meadowfoam seed oil | 0.15 | 0.15 | 0.060 |
| A | benzyl alcohol | 0.30 | 0.30 | 0.120 |
| B | de-water | 4.30 | 4.30 | 1.720 |
| C | xanthan gum | — | — | 0.001 |
| C | 1,3-butylene glycol | 6.40 | 6.40 | 2.560 |
| C | glycerine USP | 6.00 | 4.00 | 2.900 |
| C | glyceryl polymethacrylate | 4.00 | 4.00 | 1.600 |
| C | methylparaben | 0.20 | 0.20 | 0.080 |
| C | sodium benzoate | 0.20 | 0.20 | 0.080 |
| C | EDTA-2Na | 0.10 | 0.10 | 0.040 |
| C | sodium hydroxide | — | — | 0.070 |
| C | alkyl acrylate/acrylic acid copolymer | — | — | 0.280 |
| C | de-water | 76.30 | 79.35 | 88.386 |
| D | dimethyconol and dimethicone | — | — | 1.700 |
| D | Merquat Plus 3330[4] | 0.05 | — | — |
| D | Pullulan-10% solution | 1.00 | — | — |
| total | | up to 100 | | |

[1]Ceteareth-12: POE(12)Cetostearyl Ether; polyethylene glycol ether of Cetearyl alcohol having R(OCH$_2$CH$_2$)$_n$OH, n (average) = 12
[2]Ceteareth-20: POE(20)Cetostearyl Ether; polyethylene glycol ether of Cettearyl alcohol having R(OCH$_2$CH$_2$)$_n$OH, n (average) = 20
[3]Ceteareth-30: POE(30)Cetostearyl Ether; polyethylene glycol ether of Cettearyl alcohol having R(OCH$_2$CH$_2$)$_n$OH, n (average) = 30
[4]Merquat Plus 3330: polyquaternium 39

For Examples 1–3, the cosmetic emulsions are made as follows:
(1) Mix (using propeller type mixer) Phase A ingredients in a suitably size vessel and heat to about 75–80° C. until the Phase A ingredients melt completely.
(2) Add the mixture of Phase A to Phase B and mix at about 75–80° C.
(3) Cool the batch mixture of A–B to about 60° C.
(4) Separately, mix Phase C ingredients at about 70° C. until uniform and cool it about 5° C.
(5) Add Phase C mixture to the batch mixture of phases A–B and mix until uniform.
(6) Separately, prepare Phase D ingredients until they dissolve completely and add to the batch mixture of phases A–C and continue to cool to about 35° C.

(7) Mixing is continued until the resulting batch mixture is uniform.

The embodiments disclosed and represented by the previous examples have many advantages. For example, the transparent micro emulsion containing specific combination of the nonionic surfactants and oily components in the present invention provide maximizing an amount of moisturizing efficacy and skin smoothness and/or improving the spreadability of the moisturizing agent to the skin, yet continue to impart a non-greasy feeling to the user.

It is understood that the foregoing detailed description of examples and embodiments of the present invention are given merely by way of illustration, and that numerous modifications and variations may become apparent to those skilled in the art without departing from the spirit and scope of the invention; and such apparent modifications and variations are to be included in the scope of the appended claims.

What is claimed is:

1. A transparent micro emulsion comprising:
    (a) two or more nonionic surfatants selected from the group consisting of polyoxyalkylene alkyl ether having the $C_{12-18}$ of alkyl substitute, polyoxyalkylene hydrogenated castor oil, and a linear or branched, mono- or tri-alkyl glyceride;
    (b) two or more oily components selected from the group consisting of hydrocarbon oils, fatty acid esters, and silicone oils;
    (c) a water soluble high molecular weight polymer; and
    (d) a cosmetically acceptable carrier comprising a polyol and water,
    wherein the sum of the concentrations of the surfactants and the oily components is less than about 6.0 wt %; and the ratio of the surfactants to the oily components is from about 2:1 to about 1:1.

2. The emulsion of claim 1, wherein at least one of the nonionic surfactants has an HLB of more than 10 and at least one of the nonionic surfactants has an HLB of less than 10.

3. The emulsion of claim 2, wherein the mean particle size of the emulsion particles have less than about 100 mμ meter.

4. The emulsion of claim 3, wherein the mean particle size of the emulsion particles have less than about 80 mμ meter.

5. The emulsion of claim 4, wherein the concentration of the surfactants is from about 0.2% to about 2%.

6. The emulsion of claim 5, wherein the emulsion further comprises a polymer material selected from the group consisting of amphoteric polymers and cationic polymers.

7. A transparent micro emulsion comprising:
    (a) two or more nonionic surfactants selected from the group consisting of polyoxyalkylene alkyl ether having the $C_{12-18}$ of alkyl substitute, polyoxyalkylene hydrogenated castor oil, and a linear or branched, mono- or tri-alkyl glyceride;
    (b) two or more oily components selected from the group consisting of hydrocarbon oils, fatty acid esters, silicone oils, and mixtures thereof;
    (c) a water-soluble high molecular weight polymer; and
    (d) a cosmetically-acceptable carrier comprising a polyol and water,
    wherein the sum of the concentration of the surfactants and the oily components is less than about 6.0 wt %; the transparent micro emulsion has an absorbance value of less than about 2 at a wave length of 340 nm.

8. The transparent micro emulsion of claim 7, wherein the sum of the concentration of the surfactants and the oily components is less than about 3.0 wt %.

9. The transparent micro emulsion of claim 8, wherein the emulsion has an absorbance value of from about 1.0 to about 1.5 at a wave length of 340 nm.

10. The transparent micro emulsion of claim 9, wherein the concentration of the surfactants is from about 0.2% to about 1.2 wt % and the ratio of the surfactant to the oily component is from about 2:1 to about 1:1.

* * * * *

UNITED STATES PATENT AND TRADEMARK OFFICE
CERTIFICATE OF CORRECTION

PATENT NO. : 6,555,119 B1
DATED : April 29, 2003
INVENTOR(S) : Mori et al.

It is certified that error appears in the above-identified patent and that said Letters Patent is hereby corrected as shown below:

Column 3,
Line 25, "absorbent" should read -- absorbance --.

Column 8,
Line 54, "diethyinicotinamide" should read -- diethylnicotinamide --.

Column 9,
Line 61, "comeum" should read -- corneum --.

Column 11,
Line 1, "2-hydroxy4" should read -- 2-hydroxy-4 --.
Line 3, "octyidimethyl" should read -- octyldimethyl --.
Line 7, "butyidibenzoylmethane" should read -- butyldibenzoylmethane --.

Column 13,
Line 20, "surfatants" should read -- surfactants --.

Signed and Sealed this

Twenty-fourth Day of June, 2003

JAMES E. ROGAN
*Director of the United States Patent and Trademark Office*